(12) United States Patent
Babrou et al.

(10) Patent No.: US 10,138,204 B2
(45) Date of Patent: Nov. 27, 2018

(54) METHOD FOR PRODUCING N-RETINOYLCYSTEIC ACID ALKYL ESTER

(71) Applicant: ARDENIA INVESTMENTS, LTD., London (GB)

(72) Inventors: Dzianis Babrou, Uppsala (SE); Maryna Budnikava, Uppsala (SE); Mikael Björklund, Uppsala (SE); Julian Aleksov, Lidingö (SE)

(73) Assignee: ARDENIA INVESTMENTS, LTD, London (GB)

( * ) Notice: Subject to any disclaimer, the term of this patent is extended or adjusted under 35 U.S.C. 154(b) by 0 days.

(21) Appl. No.: 16/003,209

(22) Filed: Jun. 8, 2018

(65) Prior Publication Data
US 2018/0290973 A1 Oct. 11, 2018

Related U.S. Application Data

(63) Continuation of application No. PCT/SE2016/051238, filed on Dec. 9, 2016.

(30) Foreign Application Priority Data

Dec. 9, 2015 (SE) ...................................... 1551615

(51) Int. Cl.
*C07C 403/22* (2006.01)
*C07D 301/32* (2006.01)
*C07D 301/00* (2006.01)

(52) U.S. Cl.
CPC .......... *C07C 403/22* (2013.01); *C07D 301/00* (2013.01); *C07D 301/32* (2013.01)

(58) Field of Classification Search
CPC .... C07C 403/22; C07D 301/00; C07D 301/32
See application file for complete search history.

(56) References Cited

U.S. PATENT DOCUMENTS

| | | |
|---|---|---|
| 4,459,404 A | 7/1984 | Frickel et al. |
| 7,321,064 B1 | 1/2008 | Cabaj et al. |
| 2003/0050343 A1 | 3/2003 | Strelchenok et al. |
| 2004/0048923 A1 | 3/2004 | Strelchenok et al. |

FOREIGN PATENT DOCUMENTS

EP 1534672 B1 6/2005

OTHER PUBLICATIONS

Arsenov, D. V.; Babitskaya, S. V.; Vashkevich, I. I. ; Dad'kov, I. D. ; Kisel', M. A. ; Kuz'mitskii, B. B.; Strel'chenok, O. A. "Modification of the antitumor effect of doxorubicin by phosphorylated retinoids conjugated to alpha-fetoprotein" In: Pharm Chem J, Dec. 2001, vol. 35, No. 12, pp. 657-660.; p. 660, left column, first paragraph.

Arsenov, D. V. ; Dad'kov, I. G. ; Kisel' M. A.; Kuz'mitskii, B. B. ; Strel'chenok, o. A. "Synthesis of N-(all-transretinoyl)doxorubicin and study of the antitumor activity of its complex with blood serum proteins" In: Pharm Chem J, Apr. 2001, vol. 35, No. 4, pp. 186-189.; p. 188, section "Experimental chemical part".

*Primary Examiner* — Timothy R Rozof
(74) *Attorney, Agent, or Firm* — Gabriela B. Tomescu, Esq.; Bergenstrahle & Partners AB

(57) ABSTRACT

A method for producing derivatives of N-retinoylaminoalkane sulfonic acid, the method comprising providing retinoic acid, chloroformate, aminoalkanesulfonic acid selected from the group consisting of cysteic acid and alkyl ester thereof, cysteinesulfinic acid and alkyl ester thereof, homocysteic acid and alkyl ester thereof, homocysteinesulfinic acid and alkyl esters thereof, taurine and derivatives thereof, and an organic solvent, and a base, mixing said components under substantial absence of oxidizing compounds thereby forming a reaction mixture comprising a liquid phase, wherein the liquid phase is one phase and the derivatives of N-retinoylaminoalkane sulfonic acid are formed in said liquid phase.

12 Claims, No Drawings

METHOD FOR PRODUCING N-RETINOYLCYSTEIC ACID ALKYL ESTER

This application is the continuation of International Application No. PCT/SE2016/051238, filed 9 Dec. 2016, which claims the benefit of Swedish Patent Application No. SE 1551615-6, filed 9 Dec. 2015, the entire contents of which are hereby incorporated by reference.

TECHNICAL FIELD

The present invention relates generally to a method for producing derivatives of N-retinoylaminoalkane sulfonic acid.

BACKGROUND ART

U.S. Pat. No. 7,030,158 discloses N-(all-trans-retinoyl)-L-cysteic acid methyl ester and N-(13-cis-retinoyl)-L-cysteic acid methyl ester. These compounds are produced by dissolving all-trans- or 13-cis-retinoic acid and triethylamine in anhydrous tetrahydrofuran, and thereafter adding acetonitrile and butyl chloroformate. After some time the obtained mixture is added to a solution of a derivative of L-cysteic acid, sodium bicarbonate, methanol, tetrahydrofuran and water. Hence, the formation of N-(13-cis-retinoyl)-L-cysteic acid methyl ester and/or N-(all-trans-retinoyl)-L-cysteic acid methyl ester is not carried out in a single phase.

It is an object of the present invention to further decrease complexity and to further simplify the process to form N-(13-cis-retinoyl)-cysteic acid alkyl ester and N-(all-trans-retinoyl)-cysteic acid alkyl ester.

A further object with the present invention is to further increase the yield. Also, the present invention significantly reduces the reaction time as a function of yield, alternatively, provides an increased yield at comparable reaction times.

SUMMARY OF INVENTION

The present invention relates to a method for producing derivatives of N-retinoylaminoalkane sulfonic acid, the method comprising mixing under substantial absence of oxidizing compounds retinoic acid, chloroformate and an aminoalkane sulfonic acid, an organic solvent and a base thereby forming a reaction mixture comprising at least a liquid phase, where the liquid phase is one phase and the derivatives of N-retinoylaminoalkane sulfonic acid are formed in said liquid phase.

The invention further encompasses a method for producing N-(13-cis-retinoyl)-cysteic acid alkyl ester, N-(all-trans-retinoyl)-cysteic acid alkyl ester or mixtures thereof comprising reacting 13-cis-retinoic acid, all-trans-retinoic acid or mixtures thereof in a reaction mixture comprising at least a one-phase liquid phase wherein a product being N-(13-cis-retinoyl)-cysteic acid alkyl ester, N-(all-trans-retinoyl)-cysteic acid alkyl ester or mixtures thereof is formed in said liquid phase, the reaction being carried out under the essential absence of oxidizing compounds.

More specifically, the invention relates to a method for producing derivatives of N-retinoylaminoalkane sulfonic acid, the method comprising providing retinoic acid, chloroformate, aminoalkane sulfonic acid selected from the group consisting of cysteic acid and alkyl ester thereof, cysteinesulfinic acid and alkyl ester thereof, homocysteic acid and alkyl ester thereof, homocysteinesulfinic acid and alkyl esters thereof, taurine and derivatives thereof, and an organic solvent, and a base, mixing said components under substantial absence of oxidizing compounds thereby forming a reaction mixture comprising at least a liquid phase, where the liquid phase is one phase and the derivatives of N-retinoylaminoalkane sulfonic acid are formed in said liquid phase.

Another aspect of the invention relates to a method for producing derivatives of N-retinoylaminoalkane sulfonic acid, the method comprising providing a) a liquid comprising a compound selected from aminoalkane sulfonic acid selected from the group consisting of cysteic acid and alkyl ester thereof, cysteinesulfinic acid and alkyl ester thereof, homocysteic acid and alkyl ester thereof, homocysteinesulfinic acid and alkyl esters thereof, taurine and derivatives thereof, an alcohol and a first base, b) retinoic acid, c) an aprotic solvent, d) a second base, and e) a chloroformate, adding the components a), b), c), d) and e) in any order to a reaction vessel thereby forming a reaction mixture comprising at least a liquid phase, mixing said reaction mixture, wherein derivative of N-retinoylaminoalkane sulfonic acid is formed in said solution under conditions characterized as being substantially free from oxidizing compounds.

According to embodiments, the invention relates to a method for producing N-(13-cis-retinoyl)-cysteic acid alkyl ester or N-(all-trans-retinoyl)-cysteic acid alkyl ester, wherein the alkyl group comprises from 1 to 4 carbon atoms, suitably from 1 to 3 carbon atoms, preferably from 1 to 2 carbon atoms, such as methyl and ethyl. According to yet another embodiment, the invention relates to a method for producing N-(13-cis-retinoyl)-cysteic acid methyl ester and/or N-(all-trans-retinoyl)-cysteic acid methyl ester. Accordingly, the alkyl group of the cysteic acid alkyl ester comprises from 1 to 4 carbon atoms, suitably from 1 to 3 carbon atoms, preferably from 1 to 2 carbon atoms, such as methyl and ethyl. According to yet another embodiment the invention relates to a method for producing the sodium salts of N-(13-cis-retinoyl)-cysteic acid alkyl ester and/or or N-(all-trans-retinoyl)-cysteic acid alkyl ester or mixtures thereof, wherein the alkyl group comprises from 1 to 4 carbon atoms, suitably from 1 to 3 carbon atoms, preferably from 1 to 2 carbon atoms, such as methyl and ethyl.

INVENTION

The present invention relates to a method for producing derivatives of N-retinoylaminoalkane sulfonic acid. The derivatives may be selected from compounds of formula 1:

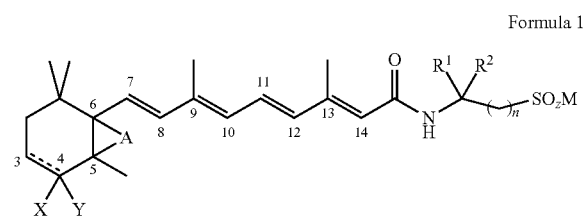

Formula 1 where n is 0-2,
Z is 2 or 3,
A is bond or oxygen atom,
X and Y are H or —OH or together =O,
a double bond between carbon atom 3 and 4 with the proviso that X and Y are H,
configuration of the double bonds between carbon atoms 9 and 10, 11 and 12, and 13 and 14—may be E- or Z-,
$R^1$ and $R^2$ are H, lower alkyls comprising from 1-4 carbon atoms, or —COOH or a pharmaceutically acceptable salt thereof, or COORS where $R^3$ is an alkyl group comprising from 1 to 4 carbon atoms,
M is a pharmaceutically acceptable cation.

Specifically preferred derivatives of N-retinoylaminoalkane sulfonic acid are N-(13-cis-retinoyl)-cysteic acid alkyl ester sodium salt and N-(all-trans-retinoyl)-cysteic acid alkyl ester sodium salt indicated by formula 2:

Formula 2

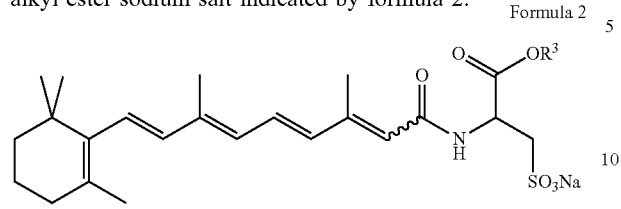

where $R^3$ is hydrocarbon comprising from 1 to 3 carbon atoms.

One of the reactants used in the method of the present invention is retinoic acid. Suitable retinoic acids may be selected from the formulas 3-6 below and indicated in table 1-4.

Formula 3

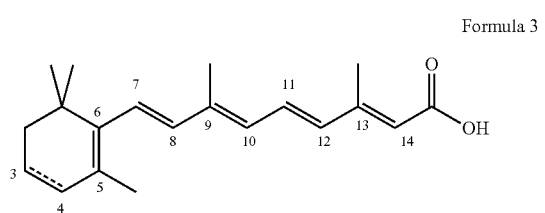

TABLE 1

| Name | Configuration of double bond | | | | 3,4-Double bond |
|---|---|---|---|---|---|
| | 13 | 11 | 9 | 7 | |
| all-trans-Retinoic acid | E | E | E | E | absent |
| 13-cis-Retinoic acid | Z | E | E | E | absent |
| 11-cis-Retinoic acid | E | Z | E | E | absent |
| 9-cis-Retinoic acid | E | E | Z | E | absent |
| 13,11-di-cis-Retinoic acid | Z | Z | E | E | absent |
| 13,9-di-cis-Retinoic acid | Z | Z | E | E | absent |
| all-trans-3,4-Didehydroretinoic acid | E | E | E | E | present |
| 13-cis-3,4-Didehydroretinoic acid | Z | E | E | E | present |

Formula 4

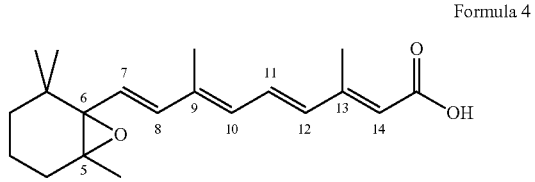

(5,6-Epoxyretinoic acids)

TABLE 2

| Name | Configuration of double bond | | | |
|---|---|---|---|---|
| | 13 | 11 | 9 | 7 |
| all-trans-5,6-Epoxyretinoic acid | E | E | E | E |
| 13-cis-5,6-Epoxyretinoic acid | Z | E | E | E |

Formula 5

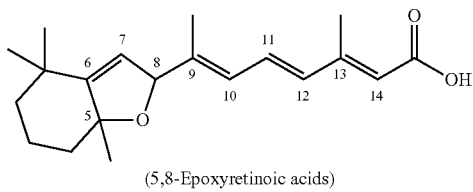

(5,8-Epoxyretinoic acids)

TABLE 3

| Name | Configuration of double bond | | |
|---|---|---|---|
| | 13 | 11 | 9 |
| all-trans-5,8-Epoxyretinoic acid | E | E | E |
| 13-cis-5,8-Epoxyretinoic acid | Z | E | E |

Formula 6

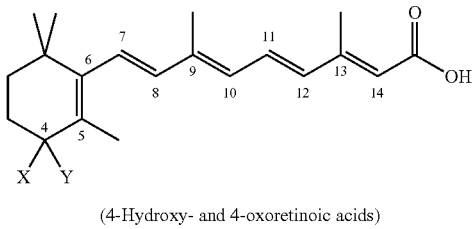

(4-Hydroxy- and 4-oxoretinoic acids)

TABLE 4

| Name | Substituents and Configuration of double bond | | | | | |
|---|---|---|---|---|---|---|
| | X | Y | 13 | 11 | 9 | 7 |
| all-trans-4-Hydroxyretinoic acid | OH | H | E | E | E | E |
| 13-cis-4-Hydroxyretinoic acid | OH | H | Z | E | E | E |
| all-trans-4-Oxoretinoic acid | O | | E | E | E | E |
| 13-cis-4-Oxoretinoic acid | O | | Z | E | E | E |

A further reactant in the method according to the invention is aminoalkanesulfonic acids. The aminoalkanesulfonic acids are selected from the group comprising cysteic acid, cysteic acid alkyl ester, cysteinesulfinic acid and alkyl ester thereof, homocysteic acid and alkyl ester thereof, and taurine and derivatives thereof. Suitable aminoalkanesulfonic acids are apparent from below formulas 7-8 and from tables 5-7.

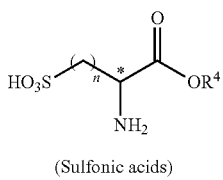

Formula 7

(Sulfonic acids)

TABLE 5

| Name | Substituents | | |
|---|---|---|---|
| | n | R⁴ | Configuration of chiral carbon (marked with asterisk) |
| Cysteic acid | 1 | H | R-, S- or rac- |
| Cysteic acid methyl ester | 1 | Me | R-, S- or rac- |
| Cysteic acid ethyl ester | 1 | Et | R-, S- or rac- |
| Homocysteic acid | 2 | H | R-, S- or rac- |
| Homocysteic acid methyl ester | 2 | Me | R-, S- or rac- |
| Homocysteic acid ethyl ester | 2 | Et | R-, S- or rac- |

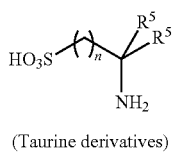

Formula 8

(Taurine derivatives)

| Name | Substituents | |
|---|---|---|
| | n | R⁵ |
| Aminomethanesulfonic acid | 0 | H |
| Taurine (2-aminoethanesulfonic acid) | 1 | H |
| 2-Amino-2-methyl-1-propanesulfonic acid | 1 | Me |
| 3-Amino-1-propanesulfonic acid (homotaurine) | 2 | H |

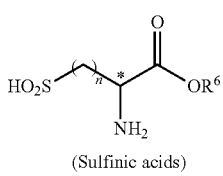

Formula 9

(Sulfinic acids)

| Name | Substituents | | |
|---|---|---|---|
| | n | R⁶ | Configuration of chiral carbon (marked with asterisk) |
| Cysteinesulfinic acid | 1 | H | R-, S- or rac- |
| Cysteinesulfinic acid methyl ester | 1 | Me | R-, S- or rac- |
| Cysteinesulfinic acid ethyl ester | 1 | Et | R-, S- or rac- |
| Homocysteinesulfinic acid | 2 | H | R-, S- or rac- |
| Homocysteinesulfinic acid methyl ester | 2 | Me | R-, S- or rac- |
| Homocysteinesulfinic acid ethyl ester | 2 | Et | R-, S- or rac- |

Further to the reactants, retinoic acid and aminoalkanesulfonic acid, chloroformate is also present in the solution. Typically, the chloroformate comprises an aliphatic group comprising from 2 to 6 carbon atoms said group preferably being iso-butyl.

The reaction is performed in a reaction mixture comprising at least one organic solvent and a base. The reaction mixture may comprise one or several different organic solvents such as protic and aprotic solvents. Alcohols are a preferred class of organic solvents. According to an embodiment, the organic solvent comprises at least one alcohol. According to yet a further embodiment, the organic solvent comprises an aprotic solvent and at least one alcohol. Usually, the alcohols are suitably monohydric alcohols comprising from 1 to 10 carbon atoms, suitably from 1 to 4 carbon atoms. Exemplified alcohols include methanol, ethanol, propanol and butanol. Suitable aprotic solvents are selected from ethers, esters, amides, nitriles, sulfoxides and mixtures thereof. Ethers are specifically preferred aprotic solvent. Examples of suitable ethers include cyclic ethers comprising 5 to 8 carbon atoms such as tetrahydrofuran.

Further to an organic solvent the reaction solution also comprises a base. The base can be one or a mixture of different bases. Typically, one type of base is used. Amines are suitable bases and preferably comprise aliphatic groups independently comprising from 1 to 4 carbon atoms. Triethylamine (TEA) is a preferred base.

The organic solvent(s), aprotic solvent(s) and base(s) are chosen and combined such that the reaction mixture comprises a liquid phase said liquid phase being one phase. The terms 'liquid phase being one phase', or 'one liquid phase' have the meaning that at least one liquid phase of the reaction mixture consists of just one liquid phase. The main chemical reaction between the retinoic acid, aminoalkane sulfonic acid and chloroformate is conducted in the at least one liquid phase said at least one liquid phase consisting of one liquid phase. Accordingly, all essential reactants (and suitably also the main product [N-retinoylaminalkane sulfonic acid]) are all essentially soluble in the at least one liquid phase of the reaction mixture and the essential reactants (retinoic acid, chloroform and aminoalkane sulfonic acid) can interact with each other without crossing a liquid-liquid phase boundary. The reaction mixture may comprise several liquid phases and solid phases as long as the reactants are all present in one liquid phase and that the main chemical reaction is conducted within the same liquid phase, said liquid phase being one phase.

According to a preferred embodiment the reaction mixture comprises essentially one liquid phase, said liquid phase having no liquid-liquid phase boundaries. The reaction mixture may comprise minor amounts of a solid phase.

According to a further embodiment the aminoalkanesulfonic acid is dissolved in an alcohol and a base is added providing a first solution. Furthermore, retinoic acid and chloroformate are dissolved in an aprotic solvent and a base is added providing a second solution comprising the reaction product of chloroformate and retinoic acid. In a further step first and second solution are mixed providing a reaction mixture comprising a liquid phase without liquid-liquid phase boundaries, where the derivative of N-retinoylaminoalkane sulfonic acid is formed in said liquid phase.

Below follows more specific embodiments within the scope of the invention without limiting the invention.

Cysteic acid alkyl ester, such as cysteic acid methyl ester, is dissolved in an alcohol and an amine. Suitable alcohols can be any alcohol capable of dissolving the cysteic acid alkyl ester such as aliphatic alcohols exemplified by aliphatic alcohols comprising form 1 to 8 carbon atoms, typically from 1 to 6 carbon atoms, e.g. methanol, ethanol, propanol, butanol, pentanol and hexanol. Ethanol and methanol is preferred. Suitable amines include aliphatic amines. The amines typically comprise the aliphatic hydrocarbons comprising independently from 1 to 6 carbon atoms, suitably from 1 to 4 carbon atoms. Suitably, the amine comprises three aliphatic hydrocarbons having same number of carbon atoms suitably from 1 to 3 carbon atoms, such as methyl, ethyl and propyl. Triethylamine (TEA) is a preferred amine. The alcohol, amine and cysteic acid alkyl ester is suitably mixed in a separate container.

13-cis-retinoic acid or all-trans-retinoic acid, or both, is charged into a reactor where suitably the temperature can be controlled, and dissolved in an organic solvent and an amine. Useful organic solvents are specifically ethers including cyclic ethers and non-cyclic ethers comprising from 4 to 10 carbon atoms. Suitable non-cyclic ethers comprise alkyl or aryl groups or both, preferably two alkyl groups. The alkyl groups may independently comprise 1 to 5 carbon atoms. Examples of suitable non-cyclic ethers are dimethyl ether, diethyl ether, dipropyl ether, and mixed ethers such as methyl ethyl ether and methyl phenyl ether. Applicable cyclic ethers are those comprising from 4 to 10 carbon atoms. Suitably, all carbon atoms from part of the ring structure. Tetrahydrofuran (THF) is a cyclic ether which can be used. Suitable amines are those which are used for dissolving the cysteic acid alkyl ester.

It is preferred that the reaction is carried out in an environment which is substantially free from oxidizing compounds. Suitably, the reactor is evacuated and filled with a gas essentially free from oxidizing compounds. Any gas can be used for filling the reactor as long as the gas is essentially free from oxidizing compounds. Suitable gases include inert gases which do not readily take part in the reactions such as nitrogen.

Furthermore, it is also advisable to carry out the main reaction and all work-up stages (which includes the work-up, additional purification stages such as chromatographic stages and subsequent evaporation/drying stages) by avoiding direct light.

Furthermore, alkyl chloroformate is mixed with an organic solvent which can be the same liquid as specified above and charged into the reactor. While adding the alkyl chloroformate to the reactor it is beneficial that the temperature is kept under room temperature, suitably from 20 to 25° C. Suitably, the temperature is maintained in the range of from a temperature where water is liquid at atmospheric pressure, from 0 up to about 15° C., suitably from about 5 to about 10° C. Generally, it is advisable that the temperature does not exceed 15° C. while adding the alkyl chloroformate. Alkyl chloroformate is added to the retinoic acid during a period of time such that the temperature of the reaction mixture (i.e. the mixture comprising the retinoic acid) does not significantly increase, such that the bulk temperature of the reaction mixture does not increase more than 10° C. Typically, the alkyl chloroformate is added within a time frame of from about 5 up to about 40 minutes, preferably between about 10 to about 25 minutes. Subsequently, the cysteic acid alkyl ester solution is charged while the reactor mixture is adjusted to ambient temperature. The reaction mixture is stirred until the reaction is finalized, usually from 1 to 5 hours and N-(13-cis-retinoyl)-cysteic acid alkyl ester and/or N-(all-trans-retinoyl)-cysteic acid alkyl ester is formed.

After completion of the reaction the reaction mixture is suitably worked-up which usually includes extraction and washing stages. The work-up may be executed as follows:

The reaction mixture is distilled off under vacuum. Thereafter an alcohol, which can be any of the alcohols disclosed above, e.g. methanol, is charged at least once after distillation. Suitably, alcohol is charged twice, the second time in combination with an ether which may be methyl tert-butyl ether (MTBE).

The reaction mixture is hereafter suitably worked up by extractions with a convenient salt solution. Many different types of salts may be used one of the being sodium chloride (NaCl). Before extraction the reaction mixture is acidified with an acid. Any acid can be used for the acidification as long as the acid is essentially free from oxidizing compounds. Suitably, acetic acid is used. The water phases are collected and further washed with an ether and/or alcohol. Usually, the water phase is washed several times with ether and/or alcohol, e.g. 2 to 5 times, typically 2 to 3 times. The ethers can be any aliphatic ether which is essentially immiscible in water such as MTBE. Suitable alcohols are aliphatic alcohols with 1 to 6 carbon atoms such as methanol and ethanol. The water phases are again collected and the organic phases discarded.

Typically, in further steps, the water phase is extracted into an ester and thereafter washed several times with a salt solution, e.g. a NaCl solution. The esters can be any aliphatic ester which is essentially immiscible in water such as ethyl acetate.

After completed work-up the product, i.e. N-(13-cis-retinoyl)-cysteic acid alkyl ester and/or N-(all-trans-retinoyl)-cysteic acid alkyl ester, is suitably further purified using chromatographic processes.

It is further preferred to additionally purify and/or concentrate the product (N-(13-cis-retinoyl)-cysteic acid alkyl ester and/or N-(all-trans-retinoyl)-cysteic acid alkyl ester) by preparative chromatographic separation processes after the work-up procedures described herein. The product may be purified/concentrated using one or more chromatographic processes/stages. Several different chromatographic separation techniques may be applied such as ion exchange chromatography, size exclusion chromatography and expanded bed adsorption chromatography. Usually, ion exchange chromatography is applied. The chromatographic processes may be run in straight phase or reverse phase. Considering that the product is provided in dissolved form, liquid chromatography is preferred. Liquid chromatography at elevated pressures, sometimes referred to as flash column chromatography, may also be contemplated. High pressure liquid chromatography (HPLC) may be chosen for purifying and/or concentrating the product. A further convenient chromatographic procedure which may be contemplated is reversed phase HPLC although also straight phase HPLC can be applied with success. Typically, the crude product, i.e. the product after work-up typically after the extraction and subsequent washings, is first chromatographically purified and subsequently chromatographically concentrated. Chromatographic purification and concentration may be carried out simultaneously in one chromatographic stage (in one and the same column), yet, often the purifying and concentration is carried out in distinctive steps in the same or different columns. Any mobile phase suitable for reversed phase chromatography can be used as long the product is sufficiently purified and/or concentrated. A suitable mobile phase can be an organic liquid which is miscible in water or at least soluble in water, exemplified by various alcohols typically monohydric alcohols, such as monohydric alcohols comprising from 1 to 6 carbon atoms. Suitably, the organic liquid is used together with a further liquid phase which can be water. If reversed phase chromatography is employed the stationary phase is hydrophobic. In the present invention, the stationary phase can be a silica based phase. Suitably, the stationary phase is a hydrocarbon modified silica, more specifically alkyl modified silica. Exemplified stationary phases suited for reversed phase chromatography include alkyl modified silica where the alkyl moiety comprises from 6 to 22 carbon atoms suitably from 8 to 20 carbon atoms, as well as silica modified by hydrocarbons comprising aromatic moieties, e.g. phenyl, and cyano modified silica. As disclosed above, the product in any state and in any degree of purity should be exposed to light as little as possible. Any form of direct light should therefore be avoided. Accordingly, the product should ideally not be exposed to light during the chromatographic procedures.

According to a further embodiment the purified product, i.e. the product which has been subjected to chromatographic purification and/or concentration, is further subjected to additional process steps. These further steps typically comprise multiple concentration/evaporation/drying stages. Before concentration/evaporation the product is dissolved in a suitable solvent which may be an alcohol suitably monohydric alcohol, or a mixture of several alcohols. Alcohols with lower boiling points are preferred as less energy must be used for evaporation. Usually, the boiling point of the alcohol, suitably monohydric alcohol, is less than about 150° C., such as less than about 100° C. Examples of alcohols include methanol, ethanol, propanol, butanol, pentanol and any isomers thereof. It is advisable to first evaporate the liquid comprising the product obtained from the chromatographic procedure and drying the residue (i.e. the product). After this initial evaporation and drying the residue is dissolved in any of the solvents presented in this paragraph and thereafter evaporated and dried. The dissolution and evaporation/drying can be repeated several times. Lastly, the dried residue comprising the product (N-(13-cis-retinoyl)-cysteic acid alkyl ester and/or N-(all-trans-retinoyl)-cysteic acid alkyl ester) is dissolved in a highly purified solvent which also may be any one of the alcohols disclosed in this very paragraph, e.g. methanol, ethanol, propanol, butanol, pentanol and isomers thereof.

EXAMPLES

Example 1

Approx. 0.8-1.2 kg cysteic acid methyl ester is dissolved in methanol and triethylamine (TEA). Approx. 0.8-1.5 kg 13-cis-retinoic acid is added to a separate reactor together with tetrahydrofurane (THF) and TEA and the reactor jacket is set to 5° C. Also, isobutyl chloroformate and tetrahydrofuran (THF) is mixed in a container and is added to the reactor at a temperature between 5-10° C. The cysteic acid methyl ester solution is then charged into the reactor which jacket temperature is adjusted to room temperature. After stirring the mixture for 3 hours the solvent is distilled off by applying vacuum. Methanol is added to the residue which is then distilled off. Methanol together with methyl tert-butyl ether (MTBE) is charged to the obtained residue. To the solution acetic acid is added and the mixture is extracted two times with a sodium chloride solution. The water phases are collected and washed three times with MTBE (7 liter in each wash). The water phases are collected in a container. The combined water phase is then extracted into ethyl acetate by charging sodium bicarbonate and charging brine and ethyl acetate to the water phase and stirring said mixture. In a final stage, the organic phase is washed several times with a sodium chloride solution comprising the addition sodium chloride solution and methanol. The water phase is discarded.

In a further step the product after extraction and washing, referred to as crude product, is further purified and concentrated using preparatory chromatographic procedures, here: High Pressure Liquid Chromatography (HPLC).

After evaporation and drying the purified product is dissolved in methanol to produce solution of N-(13-cis-retinoyl)-cysteic acid methyl ester.

Example 2.
N-(all-trans-5,6-epoxyretinoyl)-L-cysteic Acid Methyl Ester Sodium Salt 5,6-epoxy-all-trans-retinoic acid (150 mg, 0.47 mmol) is dissolved in 3 mL anhydrous THF followed by the addition of 0.07 mL of triethylamine. The obtained mixture is chilled to ca. −10° C. and 0.07 mL of isobutyl chloroformate is added under stirring. In a separate flask 0.12 g of L-cysteic acid methyl ester is dissolved in 2 mL methanol in the presence of 0.14 mL of trimethylamine. The obtained solution is added to the stirred mixture containing mixed anhydride of the 5,6-epoxyretinoic acid. The obtained solution is stirred for 3 hours at room temperature and then subjected to work up in a usual manner. The obtained crude product is purified on RP-18 silica using MeOH-water mixture as eluent to give 175 mg of the product. After purification, 5,6-epoxy-epoxyretinoyl)-L-cysteic acid methyl ester sodium salt, obtained as an oil, was dissolved in methanol and stored under argon in a freezer NMR and High resolution Mass Spectrum the purified product corresponded to the expected structure.

Example 3. N-(9-cis-retinoyl)-L-cysteic Acid Methyl Ester Sodium Salt 9-cis-retinoic acid (50 mg, 0.17 mmol) is dissolved in 0.5 mL anhydrous THF followed by the addition of 0.035 mL of triethylamine. The obtained mixture is chilled to ca. −10° C. and 0.033 mL of isobutyl chloroformate is added under stirring. In a separate flask 0.09 g of L-cysteic acid methyl ester is dissolved in 2 mL methanol in the presence of 0.14 mL of trimethylamine. The obtained solution is added to the stirred mixture containing mixed anhydride of the 9-cis-retinoic acid. The obtained solution is stirred for 3 hours at room temperature and then subjected to work up in a usual manner. The obtained crude product is purified on RP-18 silica using MeOH-water mixture as eluent to give 60 mg of the product as a yellow oil. After purification, N-(9-cis-retinoyl)-L-cysteic acid methyl ester sodium salt was dissolved in methanol and stored under argon in a freezer NMR and High resolution Mass Spectrum the purified product corresponded to the expected structure.

Example 4. N-(13-cis-5,8-epoxyretinoyl)-L-cysteic Acid Methyl Ester Sodium Salt 13-cis-5,8-epoxy-retinoic acid (150 mg, 0.47 mmol) is dissolved in 2.5 mL anhydrous THF followed by the addition of 0.07 mL of triethylamine. The obtained mixture is chilled to ca. −10° C. and 0.07 mL of isobutyl chloroformate is added under stirring. In a separate flask 0.12 g of L-cysteic acid methyl ester is dissolved in 2 mL methanol in the presence of 0.14 mL of trimethylamine. The obtained solution is added to the stirred mixture containing mixed anhydride of the 13-cis-5,8-epoxyretinoic acid. The obtained solution is stirred for 3 hours at room temperature and then subjected to work up in a usual manner. The obtained crude product is purified on RP-18 silica using MeOH-water mixture as eluent to give 170 mg of the product as a colorless oil. After purification, N-(5,8-epoxy-epoxyretinoyl)-L-cysteic acid methyl ester sodium salt was dissolved in methanol and stored under argon in a freezer NMR and High resolution Mass Spectrum the purified product corresponded to the expected structure.

The invention claimed is:

1. A method for producing derivatives of N-retinoylaminoalkane sulfonic acid, the method comprising providing
   i) a first solution comprising an aminoalkane sulfonic acid selected from the group consisting of cysteic acid and alkyl ester thereof, cysteinesulfinic acid and alkyl ester thereof, homocysteic acid and alkyl ester thereof, homocysteinesulfinic acid and alkyl esters thereof, taurine and derivatives thereof, an alcohol selected from aliphatic alcohols comprising 1 to 4 carbon atoms and a first base selected from trialkylamines,
   ii) a second solution comprising a retinoic acid, a chloroformate, an aprotic solvent and a second base, adding first and second solutions in any order to a reaction vessel thereby forming a reaction mixture comprising at least a liquid phase being one phase, mixing said reaction mixture, wherein retinoic acid, aminoalkane sulfonic acid and chloroformate are all soluble and present in said liquid phase and the derivatives of N-retinoylaminoalkane sulfonic acid are formed in said liquid phase under conditions characterised as being substantially free from oxidizing compounds.

2. The method according to claim 1, wherein the derivatives of N-retinoylaminoalkane sulfonic acid are selected from N-(13-cis-retinoyl)-cysteic acid alkyl ester and N-(all-trans-retinoyl)-cysteic acid alkyl ester, the retinoic acid is selected from 13-cis-retinoic acid or all-trans-retinoic acid, and the aminoalkanesulfonic acid selected from cysteic acid alkyl ester.

3. The method according to claim 1, wherein the alcohol is selected from the group consisting of methanol or ethanol or a mixture thereof.

4. The method according to claim 1, wherein the aprotic solvent is tetrahydrofuran.

5. The method according to claim 1, wherein the chloroformate comprises an aliphatic group comprising from 2 to 6 carbon atoms.

6. The method according to claim 1, wherein the chloroformate is iso-butyl chloroformate.

7. The method according to claim 1, wherein the second base is an amine.

8. The method according to claim 7, wherein the amine is trialkylamine, suitably triethylamine.

9. The method according to claim 1, wherein the single phase is one phase without phase separation.

10. The method according to claim 1, wherein the derivatives of N-retinoylaminoalkane sulfonic acid are purified using preparative chromatography.

11. The method according to claim 1, wherein the alkyl group of the derivatives of N-retinoylaminoalkane sulfonic acid and the alkyl of aminoalkane sulfonic acid comprises from 1 to 3 carbon atoms.

12. The method according to claim 11, wherein the alkyl group is methyl.

* * * * *